(12) United States Patent
Yanagihara et al.

(10) Patent No.: US 10,335,243 B2
(45) Date of Patent: Jul. 2, 2019

(54) DRAPE UNIT (71) Applicant: OLYMPUS CORPORATION, Tokyo (JP)

(72) Inventors: Masaru Yanagihara, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/804,025

(22) Filed: Nov. 6, 2017

(65) Prior Publication Data

US 2018/0078325 A1 Mar. 22, 2018

Related U.S. Application Data (63) Continuation of application No. PCT/JP2015/082622, filed on Nov. 19, 2015.
(Continued)

(51) Int. Cl.
*B32B 3/24* (2006.01)
*A61B 46/10* (2016.01)
(Continued)

(52) U.S. Cl.
CPC ........ *A61B 46/10* (2016.02); *A61B 17/00234* (2013.01); *A61B 17/29* (2013.01); *A61B 17/3423* (2013.01); *A61B 18/1492* (2013.01); *A61B 34/30* (2016.02); *A61B 34/32* (2016.02); *A61B 34/37* (2016.02); *A61B 34/70* (2016.02); (Continued)

(58) Field of Classification Search
CPC .............................. B32B 3/266; A61B 46/10
See application file for complete search history.

(56) References Cited

U.S. PATENT DOCUMENTS 5,386,816 A 2/1995 Inoue et al.
5,681,322 A 10/1997 Hartigan, Jr.
(Continued)

FOREIGN PATENT DOCUMENTS

CN 101416867 A 4/2009
EP 1 547 514 A1 6/2005
(Continued)

OTHER PUBLICATIONS

International Search Report dated Jan. 12, 2016 issued in International Application No. PCT/JP2015/082118.
(Continued)

*Primary Examiner* — William P Watkins, III
(74) *Attorney, Agent, or Firm* — Scully, Scott, Murphy & Presser, P.C.

(57) ABSTRACT

To keep a clean area separated from an unclean area, a drape unit for separating the manipulator that has a treatment section at a distal end of an elongated section and that has at a proximal end a proximal-end drive unit from the base including, on a substantially horizontal top surface, a drive source to which the proximal-end drive unit is detachably connected, the drape unit includes: a drape main body that has an opening from which the drive source is exposed; and an adaptor that is interposed between the drive source and the proximal-end drive unit, that is disposed with a gap vertically above the opening, and that covers the entire opening, the adaptor includes a force transmission unit for transmitting the driving force from the drive source to the proximal-end drive unit.

9 Claims, 11 Drawing Sheets

Related U.S. Application Data (60) Provisional application No. 62/168,987, filed on Jun. 1, 2015.

(51) Int. Cl.

| | | |
|---|---|---|
| A61B 34/32 | (2016.01) | |
| A61B 34/37 | (2016.01) | |
| A61B 34/00 | (2016.01) | |
| A61B 90/00 | (2016.01) | |
| A61B 17/29 | (2006.01) | |
| B25J 3/00 | (2006.01) | |
| B25J 13/02 | (2006.01) | |
| A61B 18/14 | (2006.01) | |
| A61B 90/50 | (2016.01) | |
| A61B 17/00 | (2006.01) | |
| A61B 17/34 | (2006.01) | |
| A61B 34/30 | (2016.01) | |
| A61M 25/00 | (2006.01) | |
| A61L 2/20 | (2006.01) | |
| B32B 3/26 | (2006.01) | |
| A61B 18/00 | (2006.01) | |
| A61M 39/08 | (2006.01) | |

(52) U.S. Cl.
CPC ............. *A61B 34/71* (2016.02); *A61B 34/74* (2016.02); *A61B 90/03* (2016.02); *A61B 90/06* (2016.02); *A61B 90/50* (2016.02); *A61L 2/206* (2013.01); *A61M 25/005* (2013.01); *A61M 25/0012* (2013.01); *A61M 25/0015* (2013.01); *B25J 3/00* (2013.01); *B25J 13/02* (2013.01); *A61B 18/1482* (2013.01); *A61B 2017/00314* (2013.01); *A61B 2017/00323* (2013.01); *A61B 2017/00477* (2013.01); *A61B 2017/00929* (2013.01); *A61B 2018/00077* (2013.01); *A61B 2018/00083* (2013.01); *A61B 2018/1412* (2013.01); *A61B 2034/301* (2016.02); *A61B 2034/302* (2016.02); *A61B 2034/306* (2016.02); *A61B 2090/034* (2016.02); *A61B 2217/005* (2013.01); *A61B 2218/007* (2013.01); *A61M 2025/0004* (2013.01); *A61M 2025/0019* (2013.01); *A61M 2039/082* (2013.01); *B32B 3/266* (2013.01); *H05K 999/99* (2013.01)

(56) References Cited

U.S. PATENT DOCUMENTS

| | | |
|---|---|---|
| 6,331,181 B1 | 12/2001 | Tierney et al. |
| 7,972,298 B2 | 7/2011 | Wallace et al. |
| 8,638,057 B2 | 1/2014 | Goldberg et al. |
| 8,720,448 B2 | 5/2014 | Reis et al. |
| 2002/0128649 A1 | 9/2002 | Bacher et al. |
| 2004/0019352 A1 | 1/2004 | Kidooka |
| 2005/0075739 A1 | 4/2005 | Nishizawa |
| 2005/0096502 A1 | 5/2005 | Khalili |
| 2005/0154439 A1 | 7/2005 | Gunderson |
| 2005/0159644 A1 | 7/2005 | Takano |
| 2005/0222495 A1 | 10/2005 | Okada et al. |
| 2005/0272975 A1 | 12/2005 | McWeeney et al. |
| 2006/0282063 A1 | 12/2006 | Gotani |
| 2007/0163597 A1 | 7/2007 | Mikkaichi et al. |
| 2008/0108443 A1 | 5/2008 | Jinno et al. |
| 2008/0193260 A1 | 8/2008 | Yokokohji et al. |
| 2008/0281155 A1 | 11/2008 | Fujikura |
| 2008/0294004 A1 | 11/2008 | Fujikura |
| 2009/0018390 A1 | 1/2009 | Honda et al. |
| 2009/0105726 A1 | 4/2009 | Sugiyama |
| 2009/0182200 A1 | 7/2009 | Golden et al. |
| 2009/0248039 A1 | 10/2009 | Cooper et al. |
| 2009/0275798 A1 | 11/2009 | Naito |
| 2009/0281378 A1 | 11/2009 | Banju et al. |
| 2009/0326319 A1 | 12/2009 | Takahashi et al. |
| 2010/0030023 A1 | 2/2010 | Yoshie |
| 2010/0170519 A1 | 7/2010 | Romo et al. |
| 2010/0298646 A1 | 11/2010 | Stellon et al. |
| 2010/0318100 A1 | 12/2010 | Okamoto et al. |
| 2010/0331856 A1 | 12/2010 | Carlson et al. |
| 2011/0040305 A1 | 2/2011 | Gomez et al. |
| 2011/0168189 A1 | 7/2011 | Cooper et al. |
| 2012/0271102 A1 | 10/2012 | Katayama |
| 2012/0289973 A1 | 11/2012 | Prisco et al. |
| 2013/0331857 A9 | 12/2013 | Prisco et al. |
| 2014/0166023 A1 | 6/2014 | Kishi |
| 2014/0188089 A1 | 7/2014 | Midgette et al. |
| 2014/0296771 A1 | 10/2014 | Naito |
| 2015/0025507 A1 | 1/2015 | Golden et al. |
| 2015/0173726 A1 | 6/2015 | Lohmeier et al. |
| 2015/0173727 A1 | 6/2015 | Lohmeier et al. |
| 2015/0173728 A1 | 6/2015 | Lohmeier et al. |
| 2015/0173729 A1 | 6/2015 | Lohmeier et al. |
| 2015/0173730 A1 | 6/2015 | Lohmeier et al. |
| 2015/0173731 A1 | 6/2015 | Lohmeier et al. |
| 2015/0173839 A1 | 6/2015 | Lohmeier et al. |
| 2015/0173840 A1 | 6/2015 | Lohmeier et al. |
| 2015/0238180 A1 | 8/2015 | Weitzner et al. |
| 2015/0297300 A1 | 10/2015 | Gomez et al. |
| 2016/0030124 A1 | 2/2016 | Kishi et al. |
| 2016/0184034 A1 | 6/2016 | Holop et al. |
| 2017/0361064 A1 | 12/2017 | Golden et al. |
| 2018/0206924 A1 | 7/2018 | Gomez et al. |

FOREIGN PATENT DOCUMENTS

| | | |
|---|---|---|
| EP | 1 902 666 A1 | 3/2008 |
| EP | 1 902 667 A1 | 3/2008 |
| EP | 2 116 174 A1 | 11/2009 |
| EP | 2 116 175 A1 | 11/2009 |
| EP | 2324789 A1 | 5/2011 |
| EP | 2 891 449 A1 | 7/2015 |
| JP | S6272091 U | 5/1987 |
| JP | H05095893 A | 4/1993 |
| JP | H07095953 A | 4/1995 |
| JP | H10276965 A | 10/1998 |
| JP | 2004344180 A | 12/2004 |
| JP | 2005103741 A | 4/2005 |
| JP | 2005/185309 A | 7/2005 |
| JP | 2005287963 A | 10/2005 |
| JP | 2006334695 A | 12/2006 |
| JP | 2007167644 A | 7/2007 |
| JP | 2007517597 A | 7/2007 |
| JP | 2007307289 A | 11/2007 |
| JP | 2007530155 A | 11/2007 |
| JP | 2008114339 A | 5/2008 |
| JP | 2008-212349 A | 9/2008 |
| JP | 2008278968 A | 11/2008 |
| JP | 2009011809 A | 1/2009 |
| JP | 2009100873 A | 5/2009 |
| JP | 2009523032 A | 6/2009 |
| JP | 2009240672 A | 10/2009 |
| JP | 2009-268889 A | 11/2009 |
| JP | 2009268592 A | 11/2009 |
| JP | 4420593 B2 | 2/2010 |
| JP | 2010035768 A | 2/2010 |
| JP | 2010525838 A | 7/2010 |
| JP | 2011509718 A | 3/2011 |
| JP | 2011072570 A | 4/2011 |
| JP | 2011072574 A | 4/2011 |
| JP | 2012070953 A | 4/2012 |
| JP | 2012152562 A | 8/2012 |
| JP | 2013034833 A | 2/2013 |
| JP | 2014028291 A | 2/2014 |
| JP | 2014111080 A | 6/2014 |
| JP | 2014121375 A | 8/2014 |
| JP | 2015006423 A | 1/2015 |
| JP | 2018-108430 A | 7/2018 |
| WO | 1997029690 A1 | 8/1997 |
| WO | 1998025666 A1 | 6/1998 |
| WO | 2005070339 A1 | 8/2005 |

(56) References Cited

FOREIGN PATENT DOCUMENTS

| WO | 2005094665 A2 | 10/2005 |
|---|---|---|
| WO | 2007041093 A1 | 4/2007 |
| WO | 2007070693 A2 | 6/2007 |
| WO | 2009037576 A2 | 3/2009 |
| WO | 2009091836 A1 | 7/2009 |
| WO | 2010055745 A1 | 5/2010 |
| WO | 2011/037394 A2 | 3/2011 |
| WO | 2012158449 A1 | 11/2012 |
| WO | 2013018927 A1 | 2/2013 |
| WO | 2014/005689 A2 | 1/2014 |
| WO | 2014/034532 A1 | 3/2014 |
| WO | 2014/129672 A1 | 8/2014 |
| WO | 2015/023840 A1 | 2/2015 |
| WO | 2014/106047 A1 | 7/2017 |

OTHER PUBLICATIONS

International Search Report dated Dec. 22, 2015 issued in International Application No. PCT/JP2015/078063.
International Search Report dated Nov. 10, 2015 issued in International Application No. PCT/JP2015/074792.
International Search Report dated Jan. 26, 2016 issued in International Application No. PCT/JP2015/082622.
International Search Report dated Jun. 28, 2016 issued in International Application No. PCT/JP2016/063786.
U.S. Office Action dated Sep. 14, 2017 issued in U.S. Appl. No. 15/375,374.
Office Action dated Jan. 30, 2018 received in U.S. Appl. No. 15/375,374.
Office Action dated Apr. 19, 2018 received in U.S. Appl. No. 15/804,068.
Office Action dated Apr. 19, 2018 received in U.S. Appl. No. 15/819,045.
Office Action dated Jun. 8, 2018 received in U.S. Appl. No. 15/824,481.
Notice of Allowance dated Feb. 4, 2019 received in U.S. Appl. No. 15/824,481.
Extended Supplementary European Search Report dated Dec. 19, 2018 in European Patent Application No. 16 80 2987.4.
Extended Supplementary European Search Report dated Mar. 1, 2019 in European Patent Application No. 15 89 4295.3.
Extended Supplementary European Search Report dated Mar. 21, 2019 in European Patent Application No. 15 89 4294.6.
Extended Supplementary European Search Report dated Mar. 18, 2019 in European Patent Application No. 15 89 4282.1.

DRAPE UNIT

CROSS-REFERENCE TO RELATED APPLICATIONS

This application is a Continuation Application of International Application No. PCT/JP2015/082622 filed on Nov. 19, 2015, which claims priority to Provisional application Ser. No. 62/168,987 filed on Jun. 1, 2015. The Contents of International Application No. PCT/JP2015/082622 and Provisional application No. 62/168,987 are hereby incorporated herein by reference in their entirety.

TECHNICAL FIELD

The present invention relates to a drape unit.

BACKGROUND ART

There is a known double-structured catheter in which, in a state where an inner catheter is inserted in an outer catheter, a joint section provided on the proximal end side of the outer catheter and a joint section provided on the proximal end side of the inner catheter are simultaneously attached to and detached from drive units that are provided side by side on a flat base (refer to, for example, PTL 1 below).

CITATION LIST

Patent Literature

{PTL 1}
U.S. Pat. No. 7,972,298

SUMMARY OF INVENTION

An aspect of the present invention is a drape unit for separating a manipulator and a base in a manipulator system, the manipulator system including the manipulator, a drive source to which the manipulator is detachably connected and which supplies a driving force for driving the manipulator to the manipulator, a base provided with the drive source at a top surface thereof and having a mechanism for moving the drive source in a horizontal direction, the drape unit comprising: a drape main body that has an opening from which the drive source is exposed and that covers the top surface of the base; and an adaptor that is interposed between the drive source and the manipulator, that moves relative to the drape main body in accordance with movement of the drive source, and that covers the entire opening.

DESCRIPTION OF EMBODIMENTS

A drape unit 43 according to an embodiment of the present invention will now be described with reference to the drawings.

Figure 1:
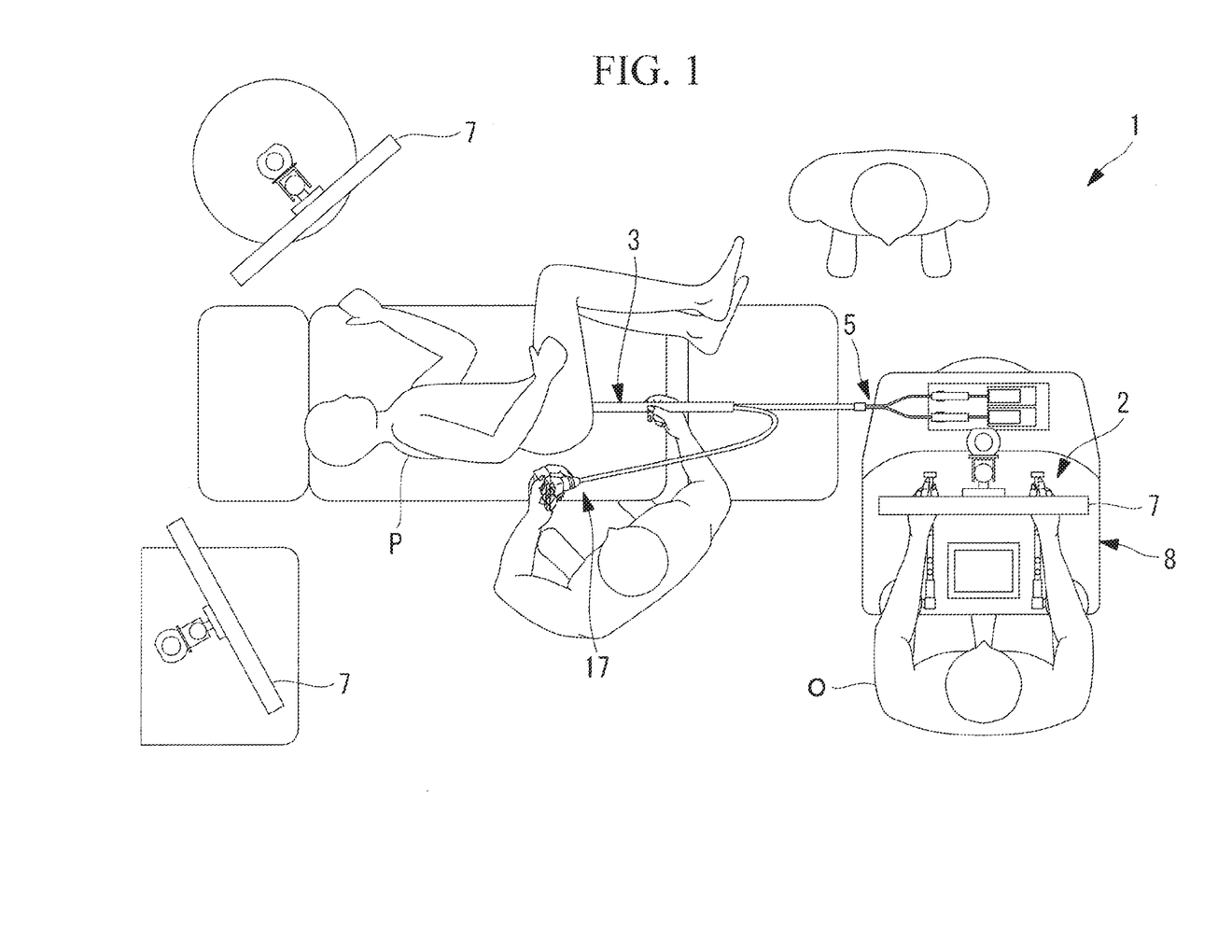
FIG. 1 is an overall structure diagram showing a medical manipulator system in which a drape unit according to one embodiment of the present invention is mounted.

The drape unit 43 according to this embodiment is mounted in a medical manipulator system 1 shown in FIG. 1 when used.

Figure 2:
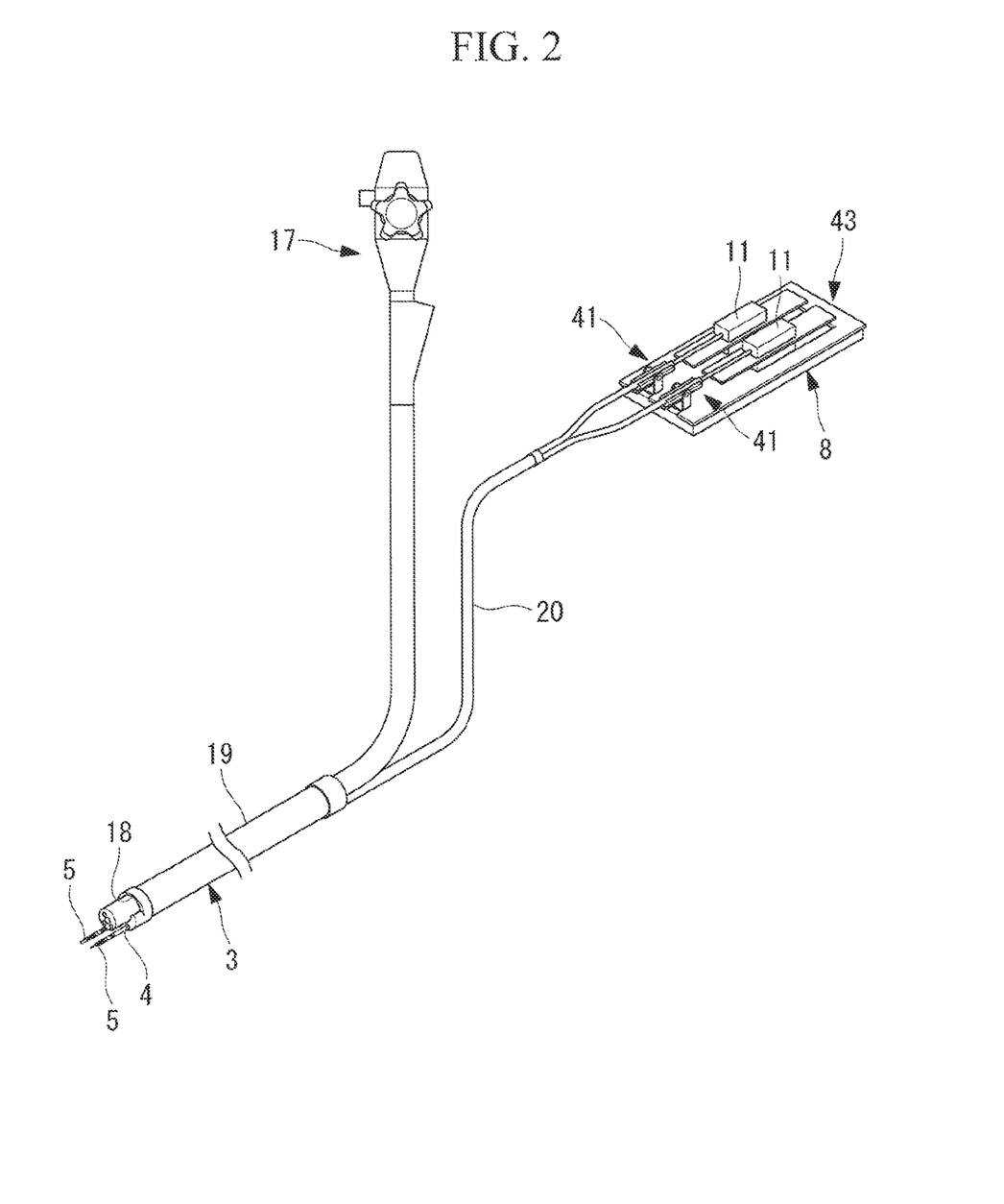
FIG. 2 is a perspective view showing a part of the medical manipulator system in FIG. 1.

As shown in FIGS. 1 and 2, the medical manipulator system 1 includes: an operation input unit 2 operated by an operator O; an overtube 3 inserted into the body of a patient P; two manipulators 5 inserted into two respective channels 4 of the overtube 3; a control unit 6 for controlling the manipulators 5 on the basis of the operation of the operation input unit 2; a monitor 7; and a console (base) 8 on which the operation input unit 2, the control unit 6, and the monitor 7 are arranged.

Figure 3:
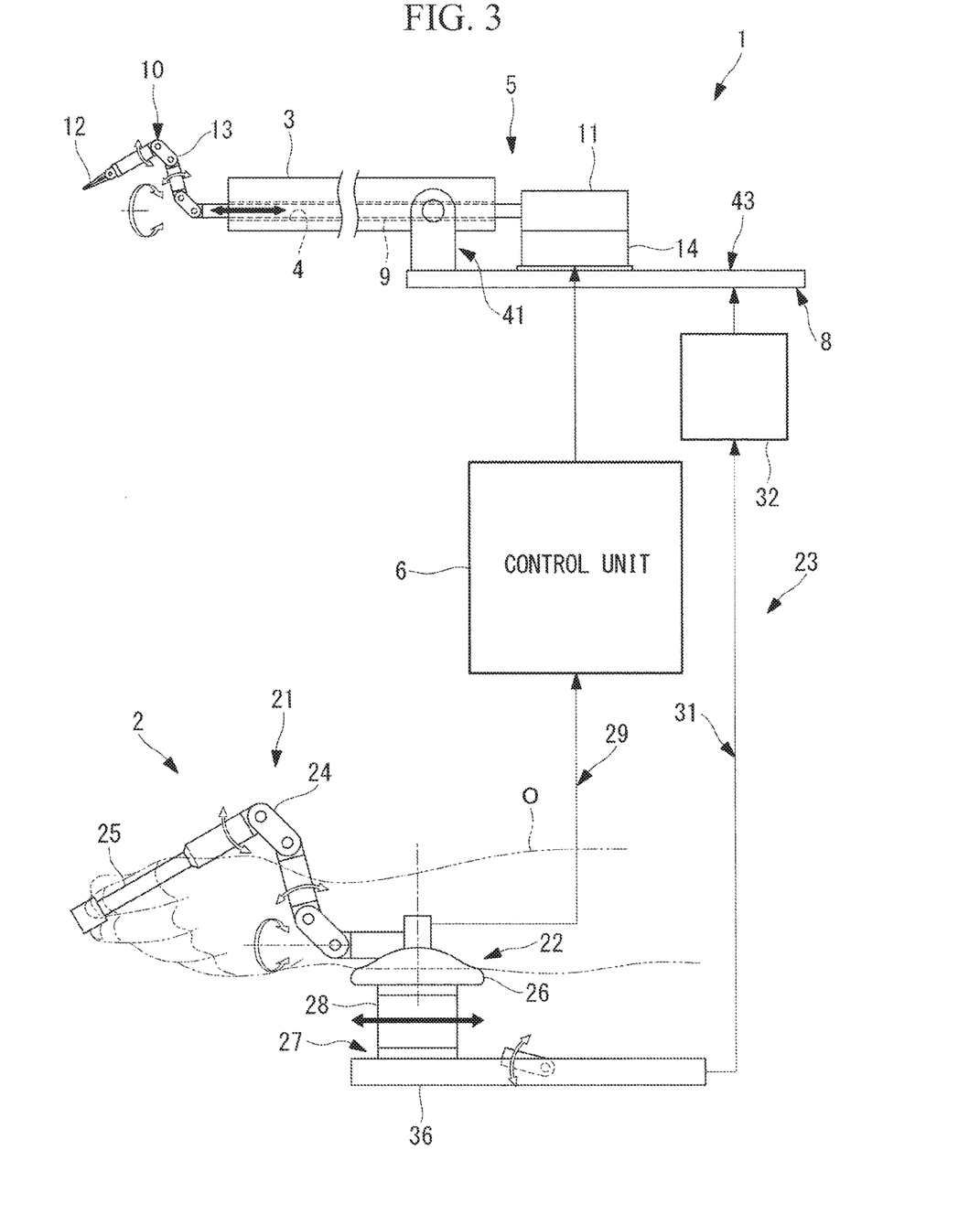
FIG. 3 is a diagram showing an operation input unit, a command transmission unit, and a manipulator of the medical manipulator system in FIG. 1.

As shown in FIG. 3, each of the manipulators 5 includes: an insertion section (elongated section) 9 inserted into the body of the patient P through the channel 4 of the overtube 3, which will be described later; a movable section 10 provided at a distal end of this insertion section 9; and a proximal-end drive unit 11 that is disposed on the proximal end side of the insertion section 9 and that drives the movable section 10 by means of a force transmission member, such as a wire, not shown in the figure.

The movable section 10 includes a treatment section 12 that is disposed at the most distal end and that works on an affected area in the body to treat the affected area; and a plurality of joints 13 for changing the distal-end position and orientation of this treatment section 12. The treatment section 12 is, for example, gripping forceps or a high frequency knife.

The proximal-end drive unit 11 is provided with an engagement tab (not shown in the figures) that is detachably connected to an engagement recess section (not shown in the figures) provided in a motor unit 14, which will be described later.

The overtube 3 is a tube formed of a flexible material and, as shown in FIG. 2, includes: a distal-end-side tubular section 19 having two manipulator channels (channels) 4 through which the respective manipulators 5 pass and a single endoscope channel 18 through which an endoscope 17 passes; and a proximal-end-side tubular section 20 that extends from the proximal end of the distal-end-side tubular section 19 so as to extend the two manipulator channels 4 towards the proximal end side and that is split into two branches on the proximal end side thereof.

As shown in FIG. 3, the operation input unit 2 includes: first operating sections 21 that are gripped and operated by the operator O with his/her hands; second operating sections 22 that are operated by the operator O with his/her wrists or arms; and a command transmission unit 23 for transmitting, to the manipulators 5, operating commands input with these operating sections 21 and 22.

Each of the first operating sections 21 has a similar shape to that of the movable section 10 of the manipulator 5, and a distal end section 25, which is supported by the same number of joints 24 as that in the movable section 10, is gripped by the operator O with his/her hand and is moved with the palm or a finger of the hand. The first operating section 21 includes a sensor, not shown in the figure, for detecting the angle of each of the joints 24 constituting this first operating section 21.

The sensor generates an electrical signal according to the angle of each of the joints 24. By doing so, each of the first operating sections 21 can input an operating command with the palm or a finger of a hand of the operator O and generate a motion command composed of electrical signals.

Each of the second operating sections 22 includes: an arm rest pedestal 26 fixed to the base of the first operating section 21; and a linear-motion mechanism 27 for integrally supporting the arm rest pedestal 26 and the first operating section 21 in a movable manner. The arm rest pedestal 26 is disposed at a position at which, when the operator O grips the distal end section 25 of the first operating section 21, the operator O can rest, on the arm rest pedestal 26, his/her arm near the wrist of the hand gripping the distal end section 25.

Figure 4:
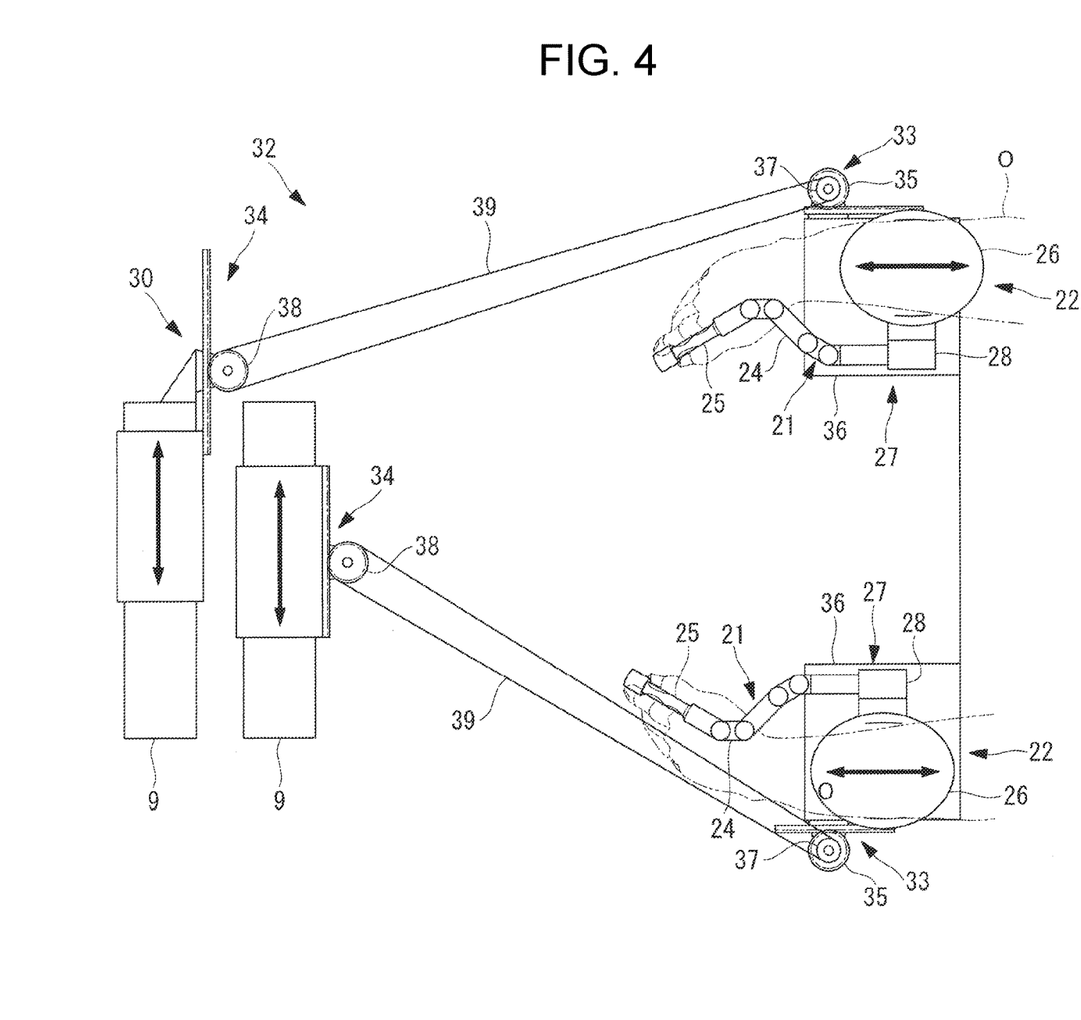
FIG. 4 is a plan view showing the operation input unit and a mechanical force transmission unit of the medical manipulator system in FIG. 1.

The linear-motion mechanism 27 includes: a slider 28 for fixing the arm rest pedestal 26 and the first operating section 21; and a linear guide 36 for supporting this slider 28 movably in a horizontal direction, as indicated by the black arrows in FIGS. 3 and 4. By moving the slider 28 in a horizontal direction with the arm resting on the arm rest pedestal 26, the position of the first operating section 21 can be moved while keeping the position/orientation at which the first operating section 21 is gripped. By doing so, the second operating sections 22 can receive, as inputs, operating commands via the wrists or the arms of the operator O and can generate motion commands on the basis of the forces input with the wrists or the arms working as mechanical driving forces of the two sliders 28.

The command transmission unit 23 includes: an electrical-signal transmission unit 29 for connecting the first operating sections 21 and the proximal-end drive units 11; and a mechanical-force transmission unit 31 for connecting the second operating sections 22 and forward/backward movement mechanisms.

The electrical-signal transmission unit 29 transmits, to the control unit 6, motion commands composed of electrical signals generated by the first operating sections 21 and supplies the command signals generated by the control unit 6 to each motor of the motor units 14. The control unit 6 calculates the amount of rotational movement and the rotational speed for each motor of the motor units 14 on the basis of the motion commands generated by the first operating sections 21, thereby controlling each motor.

As shown in FIG. 4, the mechanical-force transmission unit 31 includes a transmission unit 32 that converts a linear motion, resulting from each of the sliders 28 of the operation input unit 2 being moved forward/backward, into a linear motion of the forward/backward movement mechanism.

The transmission unit 32 includes: first rack and pinion mechanisms 33 for converting the amount of linear movement of the sliders 28 of the operation input unit 2 into rotational angles; second rack and pinion mechanisms 34 for converting the rotational motion into the amount of linear movement of the forward/backward movement mechanisms; pulleys 37 and 38 fixed to respective pinion gears 35 of these rack and pinion mechanism 33 and 34; and belts 39 wrapping around these pulleys 37 and 38.

Note that a member for electrically transmitting motive power may be employed, instead of the mechanical force transmission unit 31.

Figure 5:
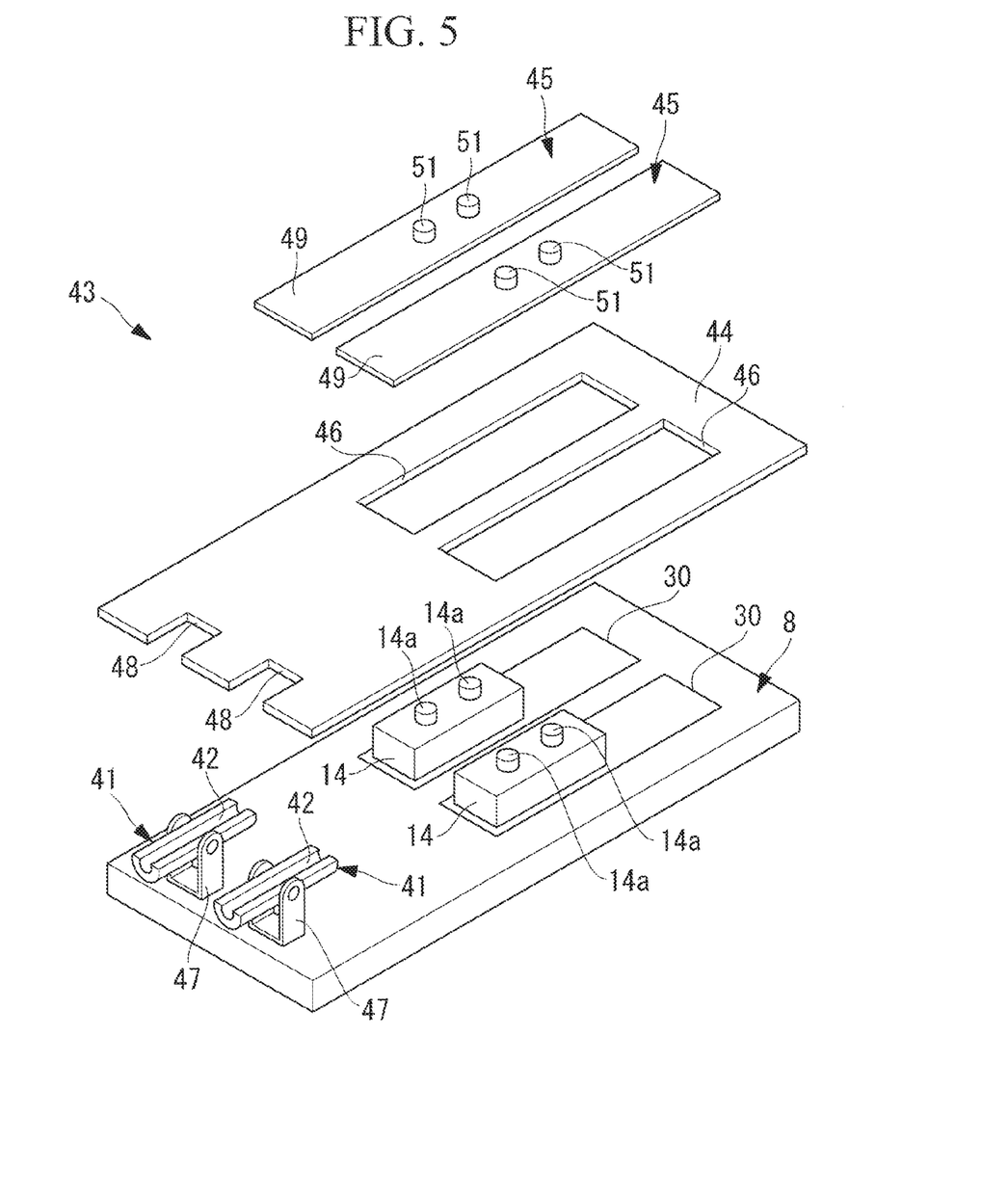
FIG. 5 is an exploded perspective view illustrating the drape unit in FIG. 1.

As shown in FIG. 5, the console 8 includes: two support sections 41 for attaching the proximal end sections of the respective proximal-end-side tubular sections 20 of the overtube 3 to a horizontally disposed planar top surface; motor units (drive sources) 14 to which the proximal-end drive units 11 of the respective manipulators 5 inserted in the overtube 3 are detachably connected and that incorporate motors for supplying motive power to the respective proximal-end drive units 11; and forward/backward movement mechanisms for causing the motor units 14 to perform linear motion.

Figure 6A:
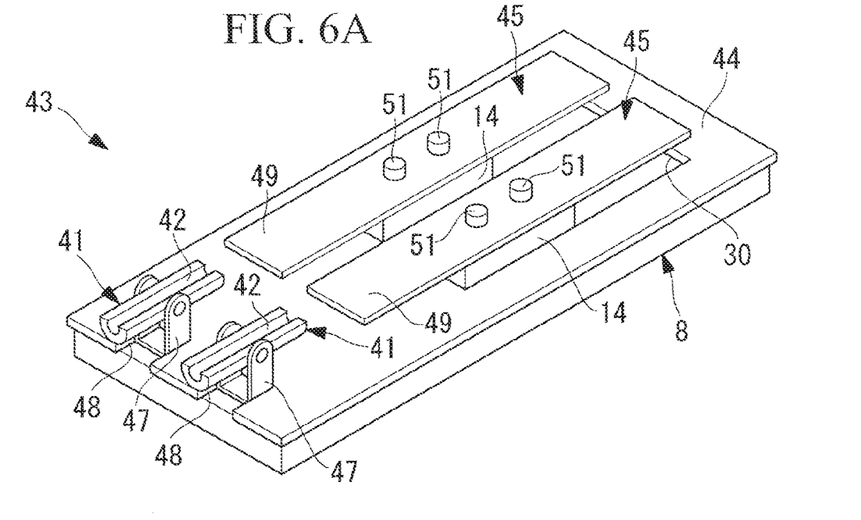
FIG. 6A is a perspective view showing a state where the drape unit in FIG. 5 is mounted on a console.
Figure 6B:
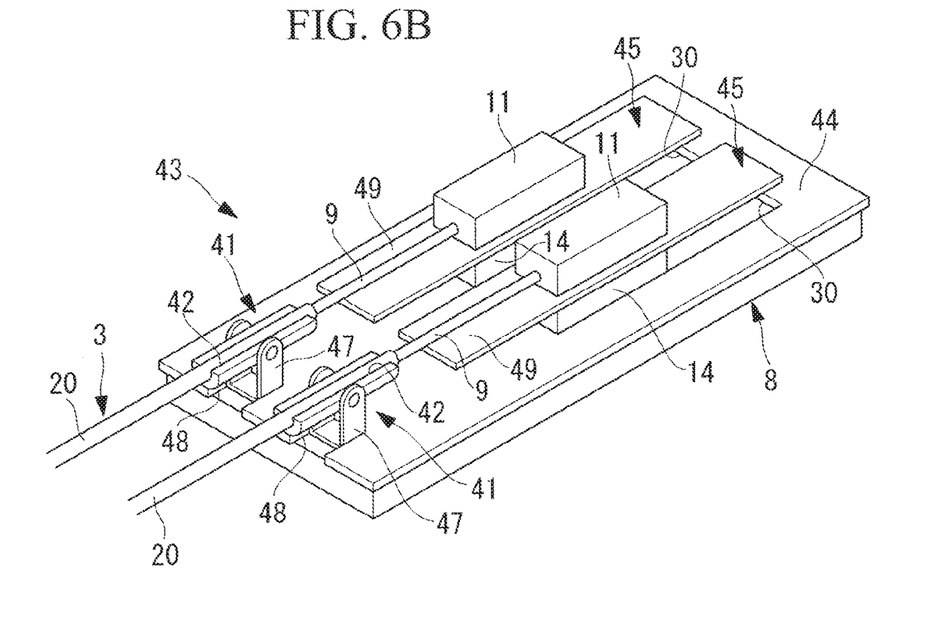
FIG. 6B is a perspective view showing a state where an overtube and manipulators are mounted after the drape unit in FIG. 6A is mounted.

As shown in FIGS. 5, 6A, and 6B, each of the support sections 41 has a structure for detachably attaching the proximal-end-side tubular section 20 of the overtube 3. For example, each of the support sections 41 has a groove 42 that becomes smaller towards the opening in transverse view, and the groove 42 can be easily attached to the overtube 3 by abutting the overtube 3 against the opening of the groove 42 and pushing the overtube 3 into the groove 42 while elastically deforming the overtube 3 or elastically deforming the support section 41.

The example in FIG. 5 shows a case where each of the motor units 14 is provided with two motors, and motor shafts 14a extend upward in the vertical direction. Connectors, not shown in the figure, are provided at the upper ends of the motor shafts 14a.

Each of the forward/backward movement mechanisms is a linear-motion mechanism, not shown in the figure, and can linearly move the motor unit 14 towards the support section 41 within the range of an opening 30 formed in the top surface of the console 8.

As shown in FIG. 5, the drape unit 43 according to this embodiment includes: a sheet-shaped drape main body 44 that is disposed so as to cover the top surface of the console 8; and adaptors 45 that are disposed so as to cover the top surfaces of the respective motor units 14 exposed on the top surface of the console 8.

The drape main body 44 includes: openings 46 that, when the drape main body 44 is disposed on the top surface of the console 8, substantially coincide with the openings 30 in the console 8 from which the motor units 14 are exposed; and notches 48 through which brackets 47 of the support sections 41 pass. The drape main body 44 is positioned on the top surface of the console 8 by making the notches 48 abut against the brackets 47. Note that each of the notches 48 does not need to be a notch but may be shaped like a hole in some cases, and the positioning may be performed by fitting the brackets 47 therein from above.

Each of the adaptors 45 includes: a flat-plate-shaped adaptor main body 49; and connection shafts 51 (force transmission units) 51 that are held in through-holes 50 penetrating through the adaptor main body 49 in the thickness direction thereof and that are rotatable about the axes of the through-holes 50.

Figure 7A:
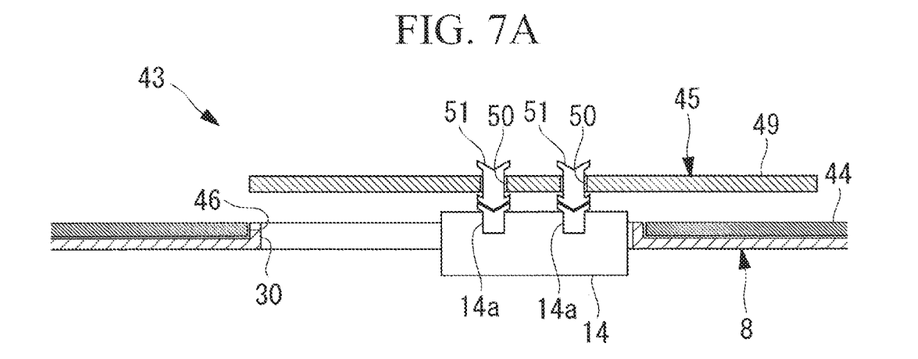
FIG. 7A is a longitudinal sectional view of the drape unit in FIG. 5, taken along a plane parallel to the direction in which a motor unit moves.
Figure 7B:
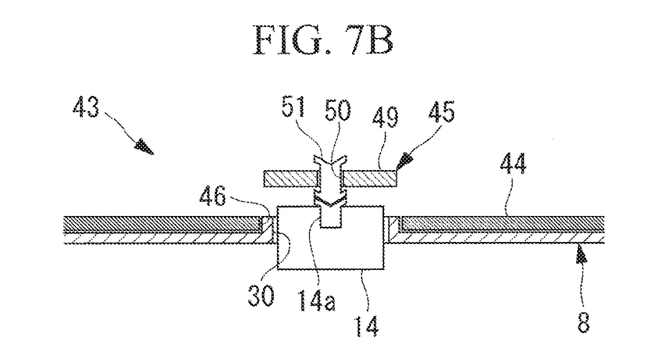
FIG. 7B is a longitudinal sectional view of the drape unit in FIG. 5, taken along a plane along the width direction of the motor unit.
Figure 7C:
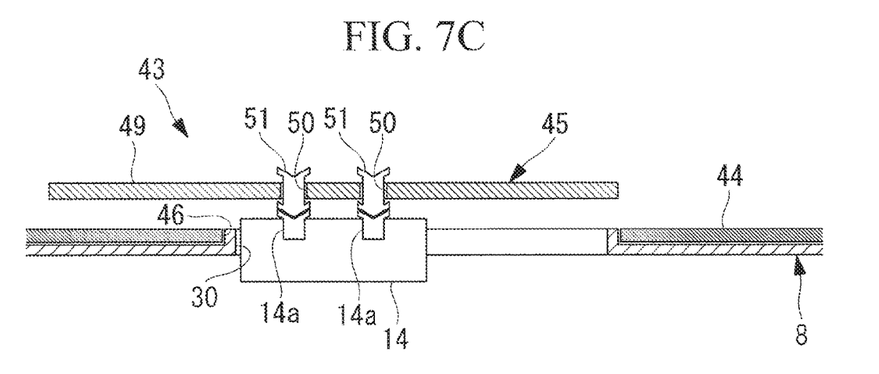
FIG. 7C is a longitudinal sectional view showing a state where the motor unit and an adaptor are moved from the state in FIG. 7A.

The adaptor main body 49 has a width dimension equal to or larger than the width dimension of the opening 46 of the drape main body 44, as shown in FIG. 7B, and has a length dimension equal to or larger than a sum of the longitudinal dimension of the opening 30 and the movement distance of the motor unit 14, as shown in FIGS. 7A and 7C.

Figure 12:
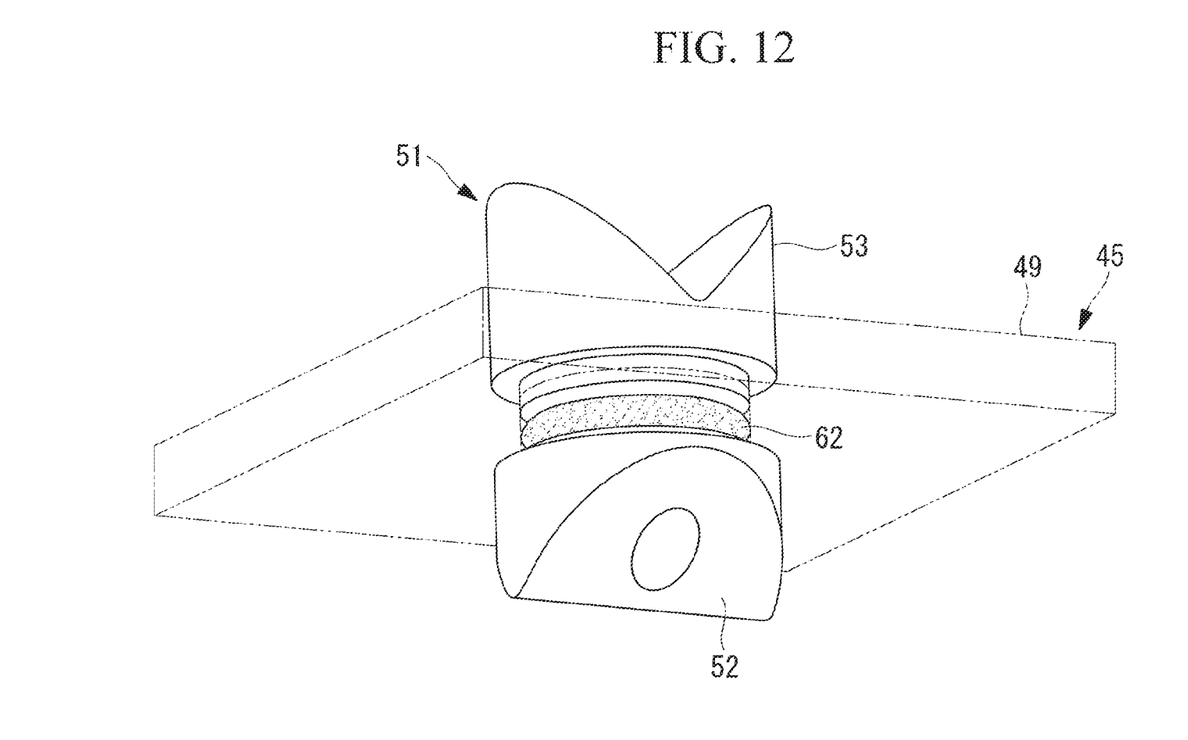
FIG. 12 is a perspective view showing one example of a connection shaft provided on an adaptor of the drape unit in FIG. 5.

As shown in FIG. 12, each of the connection shafts 51 includes at one end thereof a first connector 52 that is connected to the connector of the motor shaft 14a of the motor unit 14 and includes at the other end thereof a second connector 53 that is connected to the proximal-end drive unit 11 of the manipulator 5.

The first connector 52 has a shape that is tapered towards its distal end, which has a shape formed, for example, by cutting the columnar connection shaft 51 along two oblique planes inclined relative to the axis of the shaft 51. The second connector 53 has a shape complementary to that of the first connector 52 and is shaped like a V-groove. The phases of the first connector 52 and the second connector 53 about the axis of the connection shaft 51 differ by 90° from each other.

As shown in FIGS. 7A to 7C, the connector of each of the motor shafts 14a has the same shape as that of the second connector 53, and the connector, not shown in the figure, of each of the proximal-end drive units 11 has the same shape as that of the first connector 52.

The operation of the drape unit 43 according to this embodiment with the above-described structure will be described below.

In order to mount the drape unit 43 according to this embodiment on the console 8 of the medical manipulator system 1, the drape main body 44 is placed so as to be positioned on the top surface of the console 8, as shown in FIG. 6A. Thereafter, the adaptors 45 are placed on the top surfaces of the motor units 14. By doing so, as shown in FIGS. 7A and 7B, the first connectors 52 of the connection shafts 51 of the adaptors 45 are connected to the connectors of the motor shafts 14a of the motor units 14, and the drape main body 44 covers the entire space vertically above the openings 30 in the top surface of the console 8.

In this state, the proximal-end-side tubular sections 20 of the overtube 3 are attached to the support sections 41, the manipulators 5 are inserted from the openings in the proximal-end surface of the overtube 3 into the manipulator channels 4, and the proximal-end drive units 11 of the manipulators 5 are connected to the motor units 14 with the adaptors 45 interposed therebetween, as shown in FIG. 6B. In this case, the proximal-end drive units 11 may be provided with engagement tabs (not shown in the figures) that are detachably connected to the engagement recess sections (not shown in the figures) formed in the adaptors 45, and the adaptors 45 may be provided with other engagement tabs (not shown in the figures) that are detachably connected to other engagement recess sections (not shown in the figures) formed in the motor units 14.

Then, in this state, the distal ends of the manipulators 5 project from the distal ends of the manipulator channels 4 of the overtube 3, as shown in FIG. 3, and are disposed adjacently to the affected area in the body cavity. Thus, the operator O operates the operation input unit 2 while confirming, on the monitor 7, an image acquired by the endoscope 17. In order to operate the operation input unit 2, the operator O grips, with both hands, the distal end sections 25 of the two first operating sections 21 constituting a pair and rests both arms on the arm rest pedestals 26 of the two second operating sections 22 constituting a pair, as shown in FIG. 4.

Thereafter, when the operator O applies a force to an arm rest pedestal 26 with one of the arms, the slider 28 to which the arm rest pedestal 26 is fixed moves in the direction of the force, and the amount of the linear movement thereof is converted into a rotational angle by the first rack and pinion mechanism 33.

The amount of the linear movement, which has been converted into a rotational angle of the first rack and pinion mechanism 33, is transmitted to the second rack and pinion mechanism 34 via the pulleys 37 and 38 and the belt 39 and is converted into the amount of linear movement for the forward/backward movement mechanism. Since the motor unit 14 is fixed to the forward/backward movement mechanism, the proximal-end drive unit 11, the elongated section 9, and the movable section 10 connected to the motor unit 14 are moved integrally along the longitudinal direction of the elongated section 9. By doing so, the treatment section 12 located at the distal end of the movable section 10 is manually moved in the forward/backward movement direction in a rough way.

In this case, as shown in FIGS. 7A to 7C, the drape unit 43 according to this embodiment affords an advantage in that because the adaptor 45 is arranged so as to cover the space over the opening 46 of the drape main body 44, spanning over the entire movement range of the motor unit 14, the manipulators 5, which approache from above when inserted into the manipulator channels 4 of the overtube 3, can be prevented from coming into contact with the motor unit 14, no matter what position the motor unit 14 is disposed at, thereby keeping the manipulators 5 and so forth clean.

Furthermore, when the motor unit 14 is linearly moved via the operation of the forward/backward movement mechanism, the motor unit 14, the adaptor 45, and the proximal-end drive unit 11 are horizontally moved in an integral manner. Because the drape main body 44 and the adaptor 45 are arranged with a gap therebetween in the vertical direction, the drape main body 44 does not move when the adaptor 45 moves, thereby preventing the drape main body 44 from being caught and damaged by movement of the motor unit 14.

When the distal end sections 25 of the first operating sections 21 gripped by the operator O with both hands are moved by the force of the palms or fingers of the hands, the amounts of movement are detected by the sensor provided on each of the joints 24 and are transmitted to the control unit 6 as electrical signals. In the control unit 6, an electrical motion command for moving each of the joints 24 of the movable sections 10 so as to correspond to the angle of each of the joints 24 detected by the sensor is calculated and is then supplied to the motors of the motor units 14 connected to the joints 24. By doing so, the distal end positions of the treatment sections 12 provided at the distal ends of the movable sections 10 are precisely moved in an electrically driven manner as instructed with the palms or fingers of the hands.

When the manipulators 5 are to be extracted from the overtube 3 after the affected area in the body has been treated as described above, the proximal-end drive units 11 of the manipulators 3 are detached from the adaptors 45 and the manipulators 5 are extracted from the overtube 3.

When the manipulators 5 are extracted from the overtube 3, a body fluid, such as blood, of the patient P may flow out of the body via the manipulator channels 4 of the overtube 3. However, because the portion vertically below the proximal-end-side tubular sections 20 of the overtube 3 is covered with the drape main body 44, it is possible to prevent the body fluid from adhering to the top surface of the console 8.

Figure 8A:
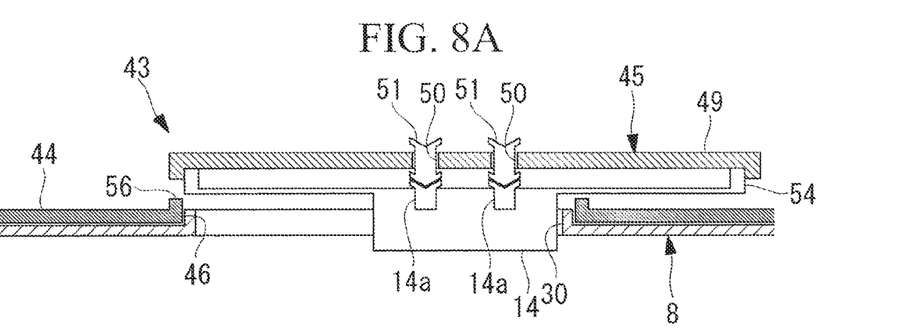
FIG. 8A is a longitudinal sectional view showing a modification of the drape unit in FIG. 5, taken along a plane parallel to the direction in which a motor unit moves.
Figure 8B:
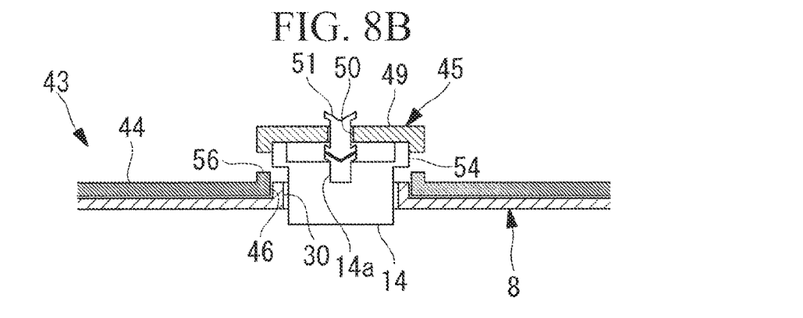
FIG. 8B is a longitudinal sectional view showing the drape unit in FIG. 8A, taken along a plane along the width direction of the motor unit.

This embodiment has been described by way of an example where each of the adaptor main bodies 49 is formed in a plate shape and maintains the horizontally extending shape thereof due to its own rigidity. Instead of this, an overhanging section 54 that extends in the form of a flange may be provided at the upper part of each of the motor units 14, and the adaptor 45 may be arranged so as to cover this overhanging section 54, as shown in FIGS. 8A and 8B. By doing so, an adaptor main body 49 formed of a less rigid material can be employed.

In this case, since each of the openings 46 of the drape main body 44 is smaller than the overhanging section 54 of the motor unit 14 disposed on the console 8, it is necessary to form the drape main body 44 of a flexible material so that when the drape main body 44 is to be mounted, the opening 46 can be pushed wide to allow the overhanging section 54 to pass therethrough.

Furthermore, in the example shown in FIGS. 8A and 8B, the drape main body 44 includes a step section 56 that rises up all around the opening 46 so as to become one step higher. By doing so, a fluid, such as a body fluid, that has been received on the top surface of the drape main body 44 can be held back by the step section 56 so as not to flow into the opening 30 in the console 8. The step section 56 may be a slope.

Figure 9A:
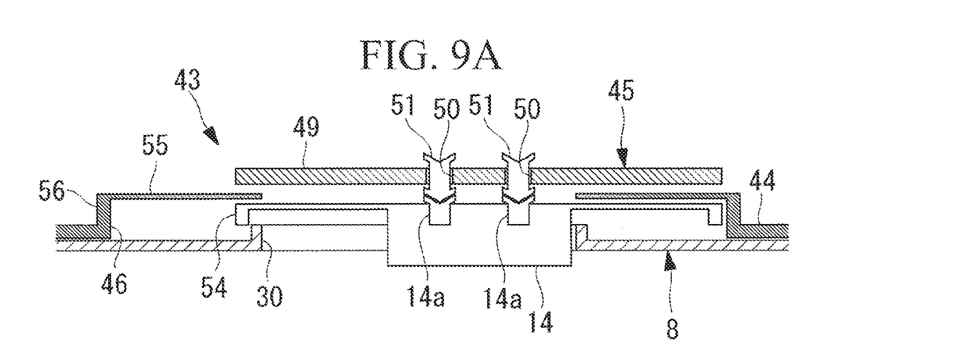
FIG. 9A is a longitudinal sectional view showing another modification of the drape unit in FIG. 5, taken along a plane parallel to the direction in which a motor unit moves.
Figure 9B:
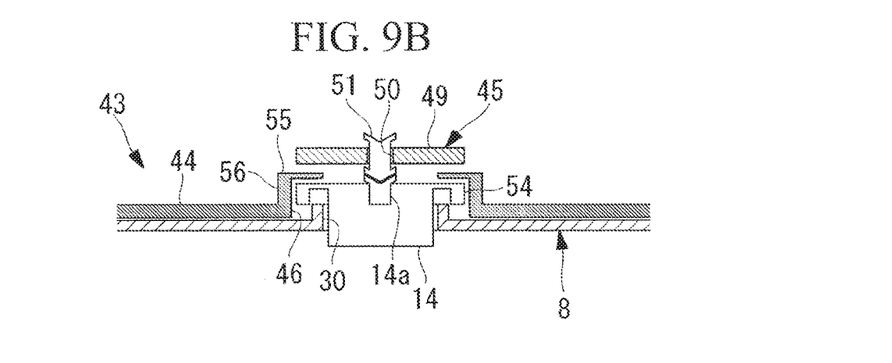
FIG. 9B is a longitudinal sectional view of the drape unit in FIG. 9A, taken along a plane along the width direction of the motor unit.

Alternatively, as shown in FIGS. 9A and 9B, the adaptor main body 49 may be formed of a more rigid material in the same manner as in FIG. 7A, a gap may be formed between the adaptor main body 49 and the overhanging section 54 of the motor unit 14, and the drape main body 44 may be provided with a flange-shaped section 55 overhanging between the adaptor main body 49 and overhanging section 54. In the example shown in the figure, as a result of the flange-shaped section 55 being provided at the upper end of the step section 56, the step section 56 can hold back a liquid effectively.

Furthermore, due to the labyrinth effect, the intricate structure of the adaptor main body 49, the flange-shaped section 55, and the overhanging section 54 prevents, for example, a fluid from easily reaching the console 8, which cannot be sterilized. Furthermore, with this structure, the drape main body 44 and the adaptors 45 can be arranged on the top surface of the console 8 from above in sequence.

Figure 10A:
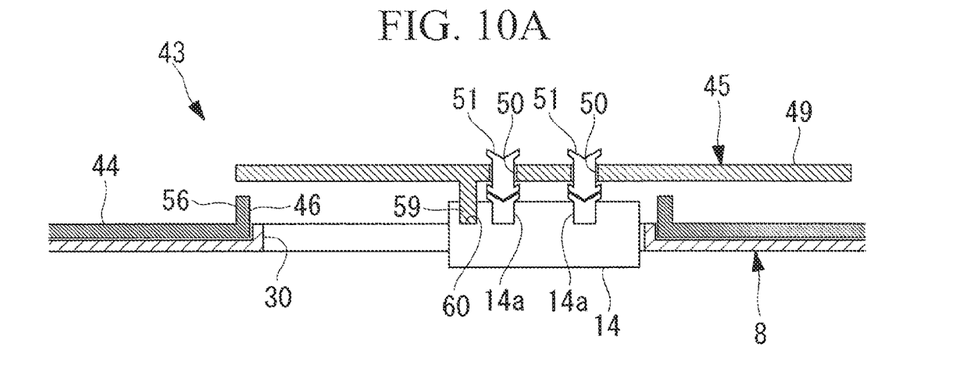
FIG. 10A is a longitudinal sectional view showing another modification of the drape unit in FIG. 5, taken along a plane parallel to the direction in which the motor unit moves.
Figure 10B:
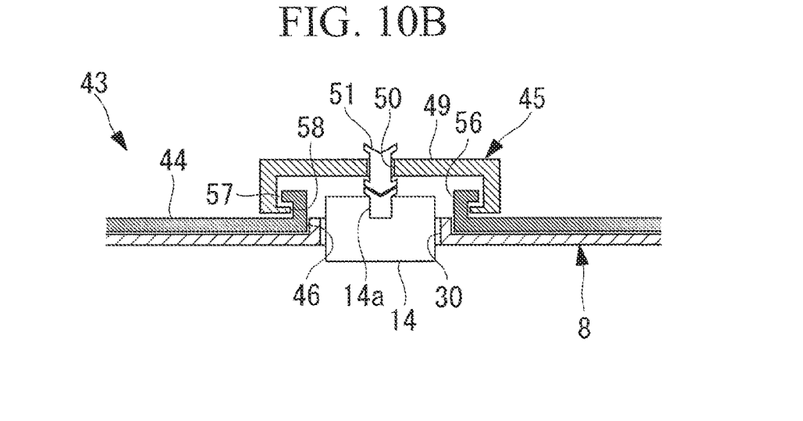
FIG. 10B is a longitudinal sectional view showing the drape unit in FIG. 10A, taken along a plane along the width direction of the motor unit.

In addition, as shown in FIG. 10B, outer collar sections 57 extending outward of the opening 46 may be provided at the upper end of the step section 56 on both ends in the width direction of the opening 46 of the drape main body 44, and the adaptor main body 49 may be provided with claw sections 58 that extend so as to wrap, from outside, the two outer collar sections 57 disposed on both sides with the opening 46 interposed therebetween. By doing so, the adaptor main body 49 is configured as an assembly that is held so that the adaptor main body 49 does not move in a direction in which the adaptor main body 49 moves away from the drape main body 44 due to the engagement between the outer collar sections 57 and the claw sections 58 but can move in a direction along the outer collar sections 57.

Furthermore, in this case, as shown in FIG. 10A, it is advisable that a positioning pin (positioning section) 59 be provided on the lower surface of each of the adaptor main bodies 49 and that a fitting hole (positioning section) 60 in which the positioning pin 59 is tightly fitted be provided on the top surface of the motor unit 14. By doing so, when the drape unit 43, configured from an assembly composed of the adaptors 45 and the drape main body 44, is placed on the top surface of the console 8 and then the positioning pins 59 are tightly fitted into the fitting holes 60, not only can the adaptor main bodies 49 be moved in a horizontal direction along with the motor units 14 via the operation of the forward/backward movement mechanisms, but also the rotational driving force from the motor units 14 can be transmitted to the connection shafts 51.

Figure 11:
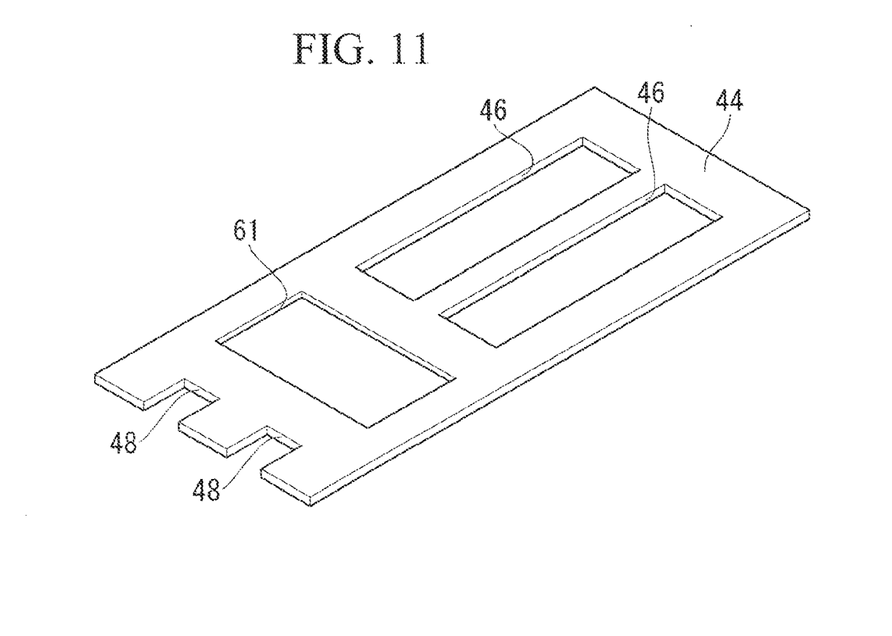
FIG. 11 is a perspective view showing a modification of a drape main body of the drape unit in FIG. 5.

Furthermore, a recess portion 61, as shown in FIG. 11, may be provided at a position that is on the top surface of the drape main body 44 and that is vertically below the proximal end sides of the support sections 41. By doing so, when the manipulators 5 are extracted from the manipulator channels 4, a body fluid, such as blood, flowing out from inside the body of the patient P via the manipulator channels 4 can be stored and prevented from flowing out externally.

Figure 13:
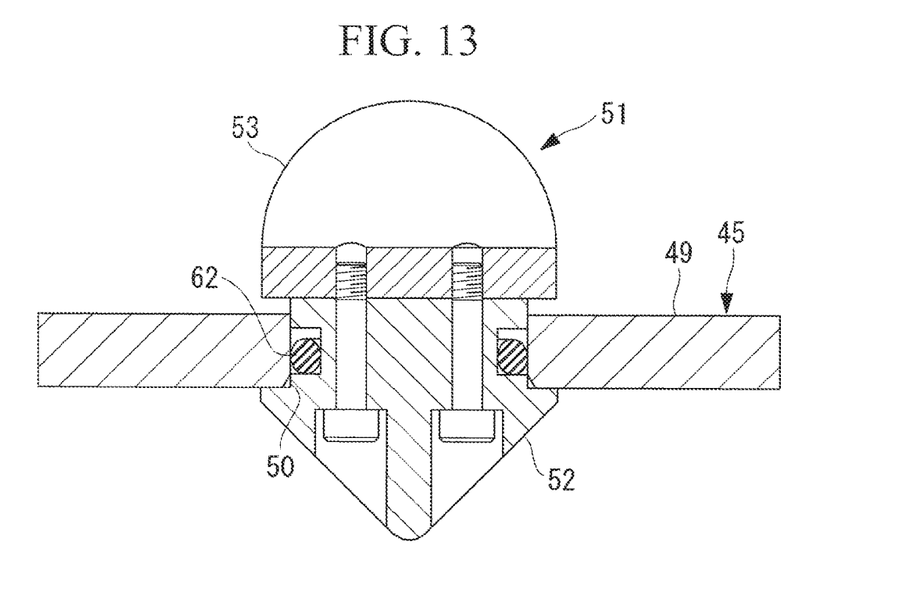
FIG. 13 is a longitudinal sectional view showing one example of a water-proofing mechanism between the connection shaft and the through-hole in the adaptor main body in FIG. 12.
Figure 14:
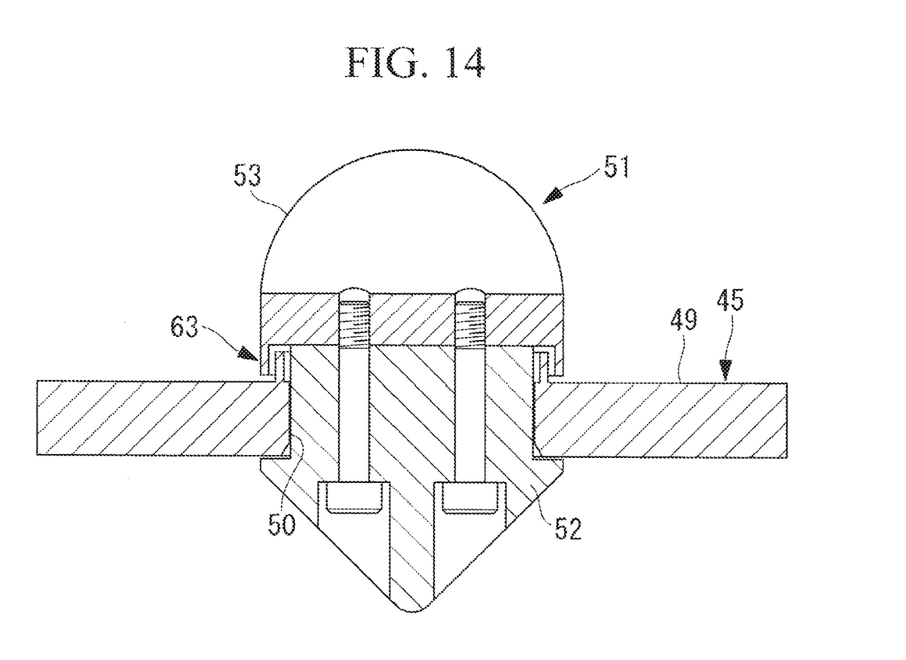
FIG. 14 is a longitudinal sectional view showing another example of the water-proofing mechanism between the connection shaft and the through-hole in the adaptor main body in FIG. 12.

Furthermore, between each of the connection shafts 51 of each of the adaptors 45 and the through-hole 50, a sealing member (water-proofing mechanism) 62, such as an O-ring, may be disposed to seal the gap therebetween all around the whole circumference thereof, as shown in FIG. 13. In addition, as shown in FIG. 14, a labyrinth structure (water-proofing mechanism) 63 formed by combining the adaptor main body 49 and the connection shaft 51 may be provided all around the through-hole 50 of the adaptor 45.

By doing so, a fluid, such as a body fluid, can be effectively prevented from flowing onto the console 8 via the gap between the connection shaft 51 and the through-hole 50.

An aspect of the present invention derived from the aforementioned embodiments is a drape unit for separating a manipulator and a base, the manipulator having a treatment section at a distal end of an elongated section and having a proximal-end drive unit for driving the treatment section at a proximal end thereof, and the base including, on a substantially horizontal top surface thereof, a drive source to which the proximal-end drive unit of the manipulator is detachably connected and which supplies a driving force to the proximal-end drive unit, the drape unit comprising: a drape main body that has an opening from which the drive source is exposed and that covers the top surface of the base; and an adaptor that is interposed between the drive source and the proximal-end drive unit, that is disposed vertically above the opening so as to form a gap between the adaptor and the opening, and that covers the entire opening, wherein the adaptor includes a force transmission unit for transmitting the driving force from the drive source to the proximal-end drive unit.

According to this aspect, as a result of the drape main body being disposed on the substantially horizontal top surface of the base, the top surface of the base is covered with the drape main body in a state where the drive source is exposed from the opening. When the proximal-end drive unit of the manipulator is connected to the exposed drive source, by connecting them through the adaptor interposed therebetween, the adaptor covers the entire opening from which the drive source is exposed. Because of this, an object, such as the manipulator, approaching from above can be prevented from coming into contact with the drive source exposed from the opening and the base, keeping the manipulator and so forth clean.

In the above-described aspect, the drive source may be provided movably in a direction along the top surface of the base, the opening may be provided so as to have a size large enough to allow the drive source to be exposed therethrough over an entire movement range of the drive source, and the adaptor may cover the entire opening wherever the drive source is positioned in its movable range.

By doing so, when the drive source is moved in a direction along the top surface of the base, the drive source, the proximal-end drive unit, and the adaptor are moved in a horizontal direction relative to the drape main body covering the top surface of the base. Because the drape main body and the adaptor are arranged with a gap therebetween in an up/down direction, the drape main body does not move, despite the movement of the adaptor, thus preventing the drape main body from being caught and damaged by the movement of the drive source. Furthermore, because the adaptor covers the entire opening, an object, such as the manipulator, approaching from above can be prevented from coming into contact with the drive source, no matter what position the drive source is placed at, thus keeping the manipulator and so forth clean.

Furthermore, in the above-described aspect, the drape main body may include a step section that protrudes upwardly all around the opening.

By doing so, an object approaching from above can be blocked, by the step section, from entering the opening. In particular, in a case where the object is a liquid, the liquid is blocked by the step section and prevented from infiltrating into the opening.

Furthermore, in the above-described aspect, an upper end of the step section may be provided with an outer collar section extending substantially parallel to a surface of the drape main body towards an outside position of the opening, and a claw section for preventing the adaptor from being detached from the drape main body may be provided on the adaptor.

By doing so, because the adaptor is kept attached to the drape main body by means of the claw section and the outer collar section, the drive source can be covered with the adaptor by placing the drape main body on the top surface of the base.

In addition, in the above-described aspect, the drape unit may further include a positioning section for positioning the drape main body to the base.

By doing so, when the drape main body is positioned on the top surface of the base, the drape main body for the base is positioned by the positioning section, and therefore, the top surface of the base can be covered easily and correctly.

Furthermore, in the above-described aspect, a surface of the drape main body, which is disposed at an upper side of the drape main body when attached to the top surface of the base, is provided with a recess portion that can store fluid.

By doing so, when the drape main body is attached to the top surface of the base, the recess portion is disposed so as to face up. If an object approaching the drape main body from above is a fluid, the fluid is stored in the recess portion. Alternatively, even if the object is not a liquid but, for example, cells, the cells are held in the recess portion so as not to scatter externally.

Furthermore, in the above-described aspect, the drape main body may include a support section for supporting a proximal end section of an overtube having a channel through which the manipulator passes.

By doing so, when the drape main body is disposed such that the top surface of the base is covered with the drape main body, the support section provided on the drape main body is disposed above the drape main body. Thus, the support section can be made to support the proximal end section of the overtube, the manipulator can be inserted into the channel, and the proximal-end drive unit of the manipulator can be connected to the drive source with the adaptor interposed therebetween.

Furthermore, in the above-described aspect, the adaptor may include: a flat-plate-shaped adaptor main body that is disposed so as to cover the opening; and a connection shaft that is held in a through-hole passing through the adaptor main body in a thickness direction thereof and that is rotatable about an axis extending in the thickness direction, wherein a rotational driving force of the drive source may be transmitted by means of rotation of the connection shaft.

By doing so, when the adaptor is attached to the drive source, the opening is blocked by the flat-plate-shaped adaptor main body, and furthermore, the rotational driving force of the drive source can be transmitted to the proximal-end drive unit by means of the connection shaft passing through the through-hole, thereby operating the treatment section.

In addition, the above-described aspect may further include a water-proofing mechanism which prevents liquid from flowing through a gap between the through-hole and the connection shaft.

By doing so, the water-proofing mechanism blocks a fluid from flowing via the gap between the through-hole and the connection shaft of the adaptor main body, thus preventing the liquid, such as a body fluid, infiltrating into areas that cannot be sterilized.

The aforementioned aspects afford an advantage in that when the manipulator is to be connected to the drive unit provided on the flat base, a clean area can be kept separated from an unclean area, despite the movement of the drive unit. Note that the drape unit according to the present invention may not be sterilized but may be merely disinfected.

REFERENCE SIGNS LIST

5 Manipulator
8 Console (base)
9 Insertion section (elongated section)
11 Proximal-end drive unit
12 Treatment section
14 Motor unit (drive source)
41 Support section
43 Drape unit
44 Drape main body
45 Adapter
46 Opening 49 Adapter main body
50 Through-hole
51 Connection shaft (force transmission unit)
56 Step section
57 Outer collar section
58 Claw section
59 Positioning pin (positioning section)
60 Fitting hole (positioning section)
61 Recessed section
62 Sealing member (water-proofing mechanism)
63 Labyrinth structure (water-proofing mechanism)

The invention claimed is:

1. A manipulator system comprising:
a manipulator having:
 an elongated portion;
 a proximal portion coupled to a proximal end of the elongated portion; and
 an end effector coupled to a distal end of the elongated portion;
a console detachably coupled to the manipulator, the console having a motor configured to generate a driving force so as to drive the end effector;
a drape configured to separate the manipulator and the console, the drape having:
 a main body configured to cover a top surface of the console, the main body having an opening so as to expose a connecting portion; and
 an adapter detachably coupled to a top surface of the motor, the adapter being configured to cover the opening;
wherein the motor is detachably coupled to the proximal portion via the adapter, and the adapter is configured to transmit the driving force from the motor to the proximal portion;
the console further having a linear-motion mechanism configured to move the motor in a horizontal direction relative to the console; and
the adapter is configured to be movable relative to the main body in response to a movement of the motor.

2. The manipulator system according to claim 1, wherein the opening has a range such that the motor can be movable by the linear-motion mechanism.

3. The manipulator system according to claim 1, wherein the main body has a flange configured to protrude upwardly all around the opening.

4. The manipulator system according to claim 3, wherein an upper end of the flange is provided with an outer collar extending substantially parallel to a surface of the main body towards an outside position of the opening, and a claw configured to prevent the adaptor from being detached from the main body is provided on the adaptor.

5. The manipulator system according to claim 1, wherein the adapter has a positioning pin configured to be fixed to the adapter and the motor.

6. The manipulator system according to claim 1, wherein the main body has a recess configured to store fluid which becomes adhered to a surface of the main body.

7. The manipulator system according to claim 1, wherein the adaptor has:
 a flat-plate-shaped main body having a hole; and
 a shaft provided to pass the hole, the shaft is configured to be rotatable relative to the flat-plate-shaped main body so as to transmit the driving force from the motor to the proximal portion.

8. The manipulator system according to claim 7, wherein the adaptor further has a water-proofing mechanism configured to prevent fluid from flowing through a gap between the hole and the shaft.

9. The manipulator system according to claim 1, wherein the console further has an operation input unit configured to operate the manipulator by an operator, and the main body of the drape is configured to cover the top surface of the console except the operation input unit.

* * * * *